United States Patent
Contracter et al.

(12) 
(10) Patent No.: US 6,281,384 B1
(45) Date of Patent: Aug. 28, 2001

(54) VAPOR PHASE CATALYTIC OXIDATION OF PROPYLENE TO ACRYLIC ACID

(75) Inventors: Rashmikant Maganlal Contracter, Wilmington, DE (US); Mark William Andersen, Charlottesville, VA (US); Jean B. Myers, Wilmington, DE (US); Gerard Hecquet, Bethune (FR); Roland Kotwica, Pontpoint (FR); Mireille Stojanovic, Paris (FR); Charlotte Pham, Saverne (FR); Michel Simon, St. Avold (FR)

(73) Assignees: E. I. du Pont Nemours and Company, Wilmington, DE (US); Atofina, Paris (FR)

( * ) Notice: Subject to any disclaimer, the term of this patent is extended or adjusted under 35 U.S.C. 154(b) by 0 days.

(21) Appl. No.: 09/105,497

(22) Filed: Jun. 26, 1998

(51) Int. Cl.$^7$ .................................................. C07L 51/235

(52) U.S. Cl. ............................................................. 562/535

(58) Field of Search .............................................. 562/535

(56) References Cited

U.S. PATENT DOCUMENTS

| | | | |
|---|---|---|---|
| 3,487,109 | 12/1969 | Kurata et al. | 260/533 |
| 3,631,099 | 12/1971 | Eden | 260/533 N |
| 3,639,269 | 2/1972 | Koberstein et al. | 252/437 |
| 3,761,424 | 9/1973 | Koberstein et al. | 252/437 |
| 3,799,979 | * 3/1974 | Hensel et al. | 260/533 |
| 3,875,220 | 4/1975 | White et al. | 260/530 N |
| 4,102,914 | 7/1978 | Beuther et al. | 260/465.3 |
| 4,152,393 | 5/1979 | Callahan et al. | 422/144 |
| 4,341,717 | 7/1982 | Callahan et al. | 260/465.3 |
| 4,442,308 | 4/1984 | Arntz et al. | 568/480 |
| 4,604,370 | 8/1986 | Sarumaru et al. | 502/38 |

(List continued on next page.)

FOREIGN PATENT DOCUMENTS

| | | | | |
|---|---|---|---|---|
| 0 034 442 | 8/1981 | (EP) | | C07C/45/34 |
| 0861819 | * 2/1998 | (EP) | . | |
| 0861821 | * 2/1998 | (EP) | . | |
| 0 861 819 A1 | * 9/1998 | (EP) | | C07C/45/28 |
| 0 861 821 A1 | * 9/1998 | (EP) | | C07C/57/04 |
| 2 227 257 | * 4/1974 | (FR) | | C07C/57/04 |
| 1307936 | 2/1973 | (GB) | | C07C/47/22 |
| 1490489 | 11/1977 | (GB) | | C07C/47/22 |
| 3-170445 | 7/1991 | (JP) | | C07C/27/12 |
| 05301051 | of 1996 | (JP) | . | |
| WO99/03809 | * 1/1999 | (WO) | | C07C/45/28 |

OTHER PUBLICATIONS

Advertising, Chemicals Technologies Worldwide, 1973.
James L. Callahan et al., Oxidation and Ammoxidation Of Propylene Over Bismuth Molybdate Catalyst, *Ind. Eng. Chem. Prod. Res. Develop.*, vol. 9, No. 2, 134–142, 1970.
Robert K. Grasselli et al., Selective Oxidation and Ammoxidation Of Propylene By Heterogeneous Catalysis, *Academic Press, Inc.*, vol. 30, 133–163, 1981.
G. S. Patience et al., Modelling Of Propylene Oxidation In A Circulating Fluidized–Bed Reactor, *Elsevier Science B. V.*, 1–18, 1994.

Primary Examiner—Gary Geist
Assistant Examiner—Robert W. Deemie

(57) ABSTRACT

An improved method for manufacturing acrylic acid by vapor phase oxidation of propylene in a single step or reaction stage using as solid phase oxidant a mixture of two particulate solids comprising a bismuth molybdate multimetal oxide (e.g., $Mo_{12}Co_{3.5}Bi_{1.1}Fe_{0.8}W_{0.5}Si_{1.4}K_{0.05}O_x$) and a molybdenum vanadate multimetal oxide (e.g., $Mo_{12}V_{4.8}Sr_{0.5}W_{2.4}Cu_{2.2}O_x$). Such a process is advantageously carried out in a recirculating solids reactor system wherein the particulate mixture of solids in an oxidized state reacts with a feed gas containing propylene in a vertical riser reactor and after separation from the acrylic acid gaseous product the particulate mixture of solids in a reduced state is regenerated by contact with an oxygen containing gas in a separate regeneration reactor before recirculation to the riser for further reaction.

8 Claims, 1 Drawing Sheet

U.S. PATENT DOCUMENTS

| | | | |
|---|---|---|---|
| 4,621,072 | 11/1986 | Arntz et al. | 502/504 |
| 4,668,802 | 5/1987 | Contractor | 549/259 |
| 4,677,084 | 6/1987 | Bergna | 502/8 |
| 4,769,477 | 9/1988 | Bergna | 549/259 |
| 5,072,052 | 12/1991 | Boeck et al. | 568/479 |
| 5,082,819 | 1/1992 | Boeck et al. | 502/212 |
| 5,519,149 * | 5/1996 | Contractor et al. | |

* cited by examiner

VAPOR PHASE CATALYTIC OXIDATION OF PROPYLENE TO ACRYLIC ACID

BACKGROUND OF THE INVENTION

1. Field of the Invention

The present invention relates to an improved vapor phase process for the catalytic oxidation of propylene to acrylic acid in a single step or stage using as oxidant a mixture of solids in an oxidized state, and where the resulting reduced solids is separately regenerated using molecular oxygen. More specifically but not by way of limitation, the invention relates to a process for performing this reaction in a recirculating solids reactor system.

2. Description of the Related Art

An important route to acrylic acid is the vapor phase oxidation of propylene over a multicomponent catalyst containing molybdenum and/or other metals, usually as their oxides. Typically, this is carried out in two steps. The first reaction step involves oxidation of propylene with air (oxygen) to form acrolein, often with a minor amount of acrylic acid, along with carbon oxides, water and smaller amounts of other oxidized byproducts. The second reaction step then converts acrolein to acrylic acid by a similar oxidation step, but typically using different reaction conditions and catalyst for optimum results.

In some proposed processes, the amount of acrylic acid co-produced with acrolein is large enough to merit isolating it as product, and recycling the acrolein back to the oxidation step. These processes typically require the separation and recycle of large amounts of acrolein.

Typically these reactions are carried out in multitubular fixed-bed reactors. The large exothermic heat of reaction and the thermal sensitivity of the propylene oxidation requires low feed concentrations, expensive heat transfer equipment, handling of a large volume of gas, and good reactor temperature control. Low propylene concentration is also required to avoid flammability conditions.

The magnitude of some of these problems is reduced when fluidized-bed reactors are used. The temperature can be readily controlled within a few degrees because of the intensive catalyst mixing and the good heat transfer characteristics. Higher propylene concentrations can be used because the danger of flammability is reduced by introducing the propylene directly into the reactor rather than pre-mixing it with air (oxygen). However, very high propylene concentrations and low oxygen-to-propylene ratios in the reactor may result in the over reduction of the solids and reduced selectivity to the desired products. Also, significant back-mixing of gases in the fluidized-bed reactor results in poorer selectivity and makes it difficult to obtain high propylene conversion.

Modified forms of fluidized-bed reactor are known as recirculating solids reactor, transport bed reactor, transport line reactor, riser reactor, fast fluidization reactor, multi-chamber fluidized bed reactor, and by other names, depending on design and/or personal preference. In this application we will use the term "transport bed reactor" to mean any reactor in which solid particles are injected at one end of the reactor and carried along with gas reactants at high velocities and discharged at the other end of the reactor to a gas-solids separation vessel. A riser reactor, in which the reactor is a vertical pipe wherein the active solids and gases are fed in at the bottom, transported in essentially plug flow and removed at the top, is one example of a transport bed reactor. Another example is a pipeline reactor, in which the flow of active solids and gases is other than vertically upwards. A transport bed reactor, as defined herein, includes a riser reactor or pipeline reactor which also incorporates a zone for fluidization, i.e., a zone where the gas velocities are sufficiently high to carry out a substantial portion of the active solids fed, but with more back-mixing of active solids than would occur in plug flow. We will use the term "recirculating solids reactor system" to mean a general reaction system with two reaction zones, in which two separate reactions take place, and which uses a particulate solid which circulates between the two reaction zones and takes part in both reactions. Optionally, either or both reaction zones may involve either a transport bed reactor or a fluidized bed. Such reaction systems have found use in catalytic cracking in petroleum refining and in other reactions.

U.S. Pat. No. 4,668,802 discloses a process for preparing maleic anhydride by oxidizing butane using an oxidized vanadium-phosphorous oxide catalyst as oxidant rather than oxygen wherein the resulting reduced catalyst is separately regenerated, and the use of a recirculating solids reactor system for this reaction. Certain of the examples use a transport bed or riser reactor for the butane oxidation reaction.

Japanese Kokai 3-170,445 discloses a similar process for preparing a mixture of acrolein and acrylic acid by oxidizing propane using an oxidized bismuth-molybdenum catalyst or vanadium pyrophosphate catalyst as oxidant. In Example 2, a propane conversion of 55%, an acrylic acid selectivity of 65%, and an acrolein selectivity of 7% were obtained using a catalyst consisting of vanadyl pyrophosphate and tellurium oxide.

An advertising folder prepared by E.I. DuPont in 1973 titled "Chemical Technologies Worldwide" included a single sheet titled "Transport Bed Reactor Technology for Selective Processes", which described the general advantages of a transport bed or riser reactor, listing among typical applications the reaction of propylene to make acrylic acid.

None of the above references disclose the necessary information to enable the economical use of a vapor phase process for the catalytic oxidation of propylene to acrylic acid in a single step or reaction stage using as oxidant a combination or mixture of catalyst in a fluidized and oxidized state, and where the resulting reduced catalyst is separately regenerated using molecular oxygen.

The preparation of multicomponent compositions containing molybdenum, vanadium and/or other metals and their use as catalysts in oxidation processes is well known in the art. For example, U.S. Pat. Nos. 4,677,084 and 4,769,477 disclose a process for making highly attrition resistant silica-based catalysts containing molybdenum, vanadium or other metals. Numerous other patents such as U.S. Pat. No. 3,487,109, U.S. Pat. No. 3,631,099, GB 1,490,489 or JP 05,301,051 also disclose specific catalyst compositions for use in the oxidation of propylene in a fixed-bed or fluidized-bed process.

BRIEF SUMMARY OF THE INVENTION

The present invention relates to a process for the selective vapor oxidation of propylene to acrylic acid in a single reaction step or single reaction stage using a mixture of bismuth molybdate multimetal oxide and molybdenum vanadate multimetal oxide each in an oxidized form or state as the oxidant. Thus the present invention provides a process for the oxidation of propylene to acrylic acid comprising the steps of: (a) contacting a feed gas comprising (i) from 1 to 100 mol % propylene, (ii) from 0 to 20 mol % oxygen, (iii) from 0 to 70 mol % water, and (vi) the remainder inert gas with an effective amount of an oxidant mixture comprising a particulate molybdenum vanadate multimetal oxide in an oxidized state and a bismuth molybdate multimetal oxide in an oxidized state at a temperature from 250 to 450° C. and for a time sufficient to convert a portion of said propylene to acrylic acid, wherein the relative amount of said molybdenum vanadate multimetal oxide is from 5 to 50 percent by weight total active ingredients and the remainder 95 to 50 percent by weight is said bismuth molybdate multimetal oxide; and (b) thereafter recovering the acrylic acid produced in step (a).

In one particular embodiment of the present invention the contacting of the feed gas and the particulate oxidant mixture in an oxidized state such as to convert the propylene to acrylic acid is performed in a transport bed reactor of a recirculating solids reactor system and wherein said particulate oxidant mixture in a reduced state after the conversion of propylene to acrylic acid is separated from the acrylic acid gaseous product and is then reoxidized in a regenerator reactor of the recirculating solids reactor system by contact with oxygen containing gas before being recirculated to the transport bed reactor. In another preferred embodiment the said transport bed reactor is a riser reactor and the particulate oxidant mixture comprises particles from 10 to 300 micron in size. Preferably in this embodiment the feed gas residence time in the riser reaction zone is from 1 second to about 15 seconds, and the particulate oxidant mixture residence time in the riser reaction zone is from 2 seconds to 120 seconds. Also, the particulate oxidant mixture residence time in the regenerator reactor is from 0.5 minute to 10 minutes and the oxygen-containing gas residence time is from 3 seconds to 30 seconds at a temperature of about 250 to about 500° C.

It is an object of this invention to provide an improved vapor phase process using a transport bed reactor for the oxidation of propylene to acrylic acid in a single step using the oxidized form of attrition resistant multimetal oxide, and where the resulting reduced solids are separately regenerated using oxygen containing gas. It is a further object of the present invention to provide a mixed multimetal oxide system that will serve as an oxidant for the vapor phase conversion of propylene to acrylic acid in a single step or reaction stage. Fulfillment of these objects and the presence and fulfillment of additional objects will become apparent upon complete reading of the specification and attached claims.

DETAILED DESCRIPTION OF THE INVENTION

Figure 2:
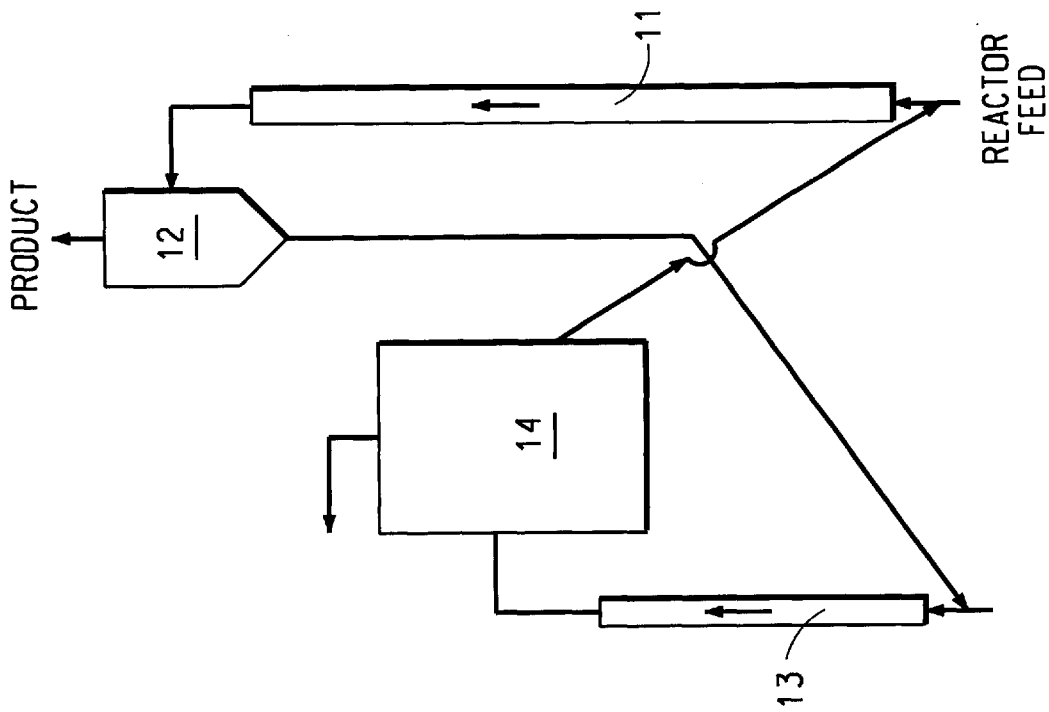
FIG. 2 is shows a schematic drawing of a recirculating solids reactor configuration in which the reaction zone is comprised of a riser section and the regeneration zone is comprised of two parts, a riser section and a fluid bed section.

The present invention relates to an improved process for the selective vapor oxidation of propylene to acrylic acid in a single reaction stage or step in a recirculating solids reactor system which includes a transport bed reactor and a separate regenerator. The transport bed reactor is preferably a riser reactor in which particles are injected at the bottom of a vertical pipe, carried upwards with gas reactants at high velocities and discharged to a gas-solids separation vessel, or a combination of a riser reactor with a fluidization zone. The reaction between gas and solids occurs in the riser pipe in a matter of seconds, as distinguished from a conventional fluidized bed reactor where the reaction time is a matter of minutes. Gas velocities in a riser reactor are about 2 to 15 times higher than in fluidized bed reactors; solids concentrations may be up to about 40 times lower. The product of the above reaction is then sent to a conventional processing unit where the acrylic acid is separated and recyclable impurities such as acrolein are returned for further processing.

The reduced solids are then reoxidized in a separate oxidation step to enable their reuse for the oxidation of propylene. The reduced solids from the riser zone are first separated from the product gas, stripped of any carbonaceous species in a separate stripper zone and then sent to the regenerator for reoxidation. This process permits independent control of the reactant gas concentrations, the gas residence time, and the solids residence time in each zone for optimum operation.

There are several advantages of the above reactive concept over the steady-state fixed bed or fluidized bed alternative. High selectivity is achieved because of plug flow and optimum oxidative state of the solids. Significant reductions are realized in product recovery costs because the regeneration off-gas stream is kept separate from the product gas stream, resulting in a highly concentrated product stream. High throughput rates are attributed to the independent control of variables for the two steps of the operation, resulting in reduced investment and decreased multimetal oxide inventory.

When a hydrocarbon oxidation reaction is carried out in the absence of molecular oxygen, lattice oxygen from the surface layers of these mixed metal oxide solids gets consumed very rapidly, typically in a matter of seconds. When that occurs, the activity of the solids decreases dramatically. If the solids are allowed to remain in the reducing atmosphere, reduced surface layers are built up on an oxidized core because diffusion of the bulk lattice oxygen to the surface is generally very slow in most practical situations. These reduced layers decrease selectivity and cause excessive yield losses when they get oxidized in the regenerator to carbon oxides. Previous proposals for the oxidation of propylene to acrylic acid using an oxidant and a separate regeneration zone for the active solids do not disclose the surprising benefit of a short residence time in the propylene oxidation/solids reduction zone.

In carrying out the inventive process, the feed gas to the propylene oxidation step contains about 1 mol % to 100 mol % propylene (preferably about 5 mol % to about 30 mol % propylene) and 0 to 30 mol % acrolein. Some of the propylene and acrolein used in the feed may be provided by the unconverted and partially converted propylene which is present in the recycled reaction gas. In some cases, propylene may be available as the predominant component in a mixture of gases including other hydrocarbons. As long as none of the other gases present significantly adversely affect the process, it may be more convenient to use this propylene-rich mixture in the feed gas as the source of propylene. The oxygen concentration in the feed gas can be from 0 to 20 mol %. Air can be used as the source of oxygen. The remainder of the feed can be any inert gas, such as nitrogen or recycled reaction gas containing mostly water, carbon monoxide and carbon dioxide, and possibly unconverted propylene and acrolein.

The present invention uses an effective mixture of a bismuth molybdate multimetal oxide and a molybdenum vanadate metal oxide in oxidized form. The weight fraction of the molybdenum vanadate multimetal oxide expressed as weight percent active ingredient in the total charge is 5 to 50%, preferably 10 to 50%, with the remainder being the relative amount of the bismuth molybdate multimetal oxide. It should be appreciated that these respective weight fractions are numerically based on active ingredient and as such do not include the mass associated with the use or presence of any solid inert support (e.g., $Al_2O_3$, $SiO_2$ or mixtures and the like) or silica additive (either derived from silicic acid, polysilicic acid, colloidal silica or combinations thereof) associated with imparting attrition resistance. Preferably these are specially hardened solids which resist attrition, such as disclosed in previously referenced U.S. Pat. Nos. 4,677,084 and 4,769,477. Numerous other bismuth molybdate metal oxide compositions are disclosed in the art for the vapor phase oxidation of propylene to acrolein, and numerous other molybdenum vanadate metal oxide compositions are disclosed in the art for the vapor phase oxidation of acrolein to acrylic acid, and are also suitable for the operation of this invention. The solid particles are preferably about 10 to about 300 micrometers in size.

The oxidation step is carried out in the reaction zone at a temperature of about 250 to about 450° C. The reactor gas exit pressure is typically 0 to 50 psig (0 to $3.95 \times 10^5$ Pa). The gas residence time in the reaction zone is typically about 1 second to about 15 seconds, and the solids residence time in the reaction zone is about 2 seconds to 120 seconds. The upper limit of solids residence time will, of course, depend on their activity. If still active, the solids can be retained in the reaction zone for longer than 120 seconds. Preferably, the solids are removed from the propylene oxidation step when the oxidative surface layer of the solids has been essentially reduced to a non-oxidized form. The solids in the reactor effluent are separated from the effluent gases, and the acrolein and acrylic acid products are recovered from the effluent gases, both separations employing conventional techniques and equipment. The separated solids are referred to herein as the reduced solids because they are in a lower oxidation state than that of the fresh solids which enters the reaction zone. When appropriate to the embodiment, the reduced solids are preferably stripped of any reactor gases and then transported to the regeneration zone of the recirculating solids reactor system. The stripped reactor gases are mixed with the reactor effluent gases. Acrylic acid and optionally acrolein are recovered from the effluent gases of the reaction zone in conventional processing units, and remaining gases may be vented or recycled to the reaction zone. Any off-gases from the regeneration zone can be vented preferably after heat recovery.

The reduced solids are reoxidized in the regeneration zone using an oxygen-containing gas such as air, oxygen enriched air or the like. Preferably the regeneration zone temperature is maintained at about 250 to about 500° C. The solids residence time in the regenerator zone is about 0.5 minute to, typically, about 10 minutes. The oxygen-containing gas residence time is about 3 seconds to about 30 seconds. Total gas flow rate and oxygen concentration must be sufficient to provide the needed oxygen for solids reoxidation to occur within the selected gas and solids residence time. The oxidized solids are then recycled to the reaction zone.

The required amount of solids and the required solids circulation rate depend on the extent to which the solids reoxidation reaction is carried out in the regeneration zone (as opposed to the reaction zone), the amount of propylene to be reacted, the amount of mobile (or reactive) oxygen contained by the solids, and the reaction zone process conditions that determine the amount of catalyst oxygen used per pass. When oxygen concentration in the reaction zone is low, or zero, and substantially all of the solids reoxidation reaction is carried out in the regeneration zone, a high catalyst circulation rate is required. This rate may be reduced, to the extent that the solids reoxidation reaction is carried out in the reaction zone.

A recirculating solids reactor system can be operated continuously to oxidize propylene without any gas-phase oxygen in the reaction zone. Such operation results in a higher selectivity to make acrylic acid than can be attained with conventional fluidized or fixed bed reactors, providing an adequate solids circulation rate is maintained to supply the needed oxidized solids. In order to minimize the gas phase oxygen in the reaction zone, gas phase oxygen is stripped from the oxidized solids before recycling them to the reaction zone.

Alternatively, if a recirculating solids reactor system is operated so as to oxidize propylene under conditions of temperature, oxygen and propylene partial pressures and residence time in the reaction zone identical to those used in conventional reactors, significantly higher conversion of propylene and significantly higher yield of acrylic acid are obtained.

The high selectivity to acrylic acid attained in the transport bed reactor is maintained even if the feed to the reaction zone has a very high propylene concentration. The gas feed can be 100% propylene.

Recirculating solids reactor systems can in general have many different reactor/regenerator configurations. For example, the reaction zone of the system can be comprised of a transport bed reactor, a fluidized bed reactor or other gas-solid reactors, as can the regeneration zone. The recirculating solids reactor system employed in this invention utilizes a transport bed reactor for the reaction zone. Optionally the transport bed reactor may comprise a riser reactor, a pipeline reactor, or a riser or pipeline reactor combined with a fluidization zone. The regeneration zone of the regenerator can be comprised of a riser reactor, a pipeline reactor, a fluidized bed reactor of any type, or a combination of the above reactors. It is to be understood that the invention is not limited to the specific combination of reactors listed above.

A transport bed reactor is characterized by high gas velocities of from about 5 ft/sec (about 1.5 m/sec) to greater than 40 ft/sec (12 m/sec). At the lower end of the velocity range there can be a significant amount of local back-mixing of solids. Typically, the reactor line is vertically mounted with gas and solids flowing upward in essentially plug flow; i.e., a riser reactor. Preferably, the superficial gas velocity in the riser is maintained at 3 to 30 feet/sec (1 to 10 meters/sec). The flow can also be downward and the reactor line can be mounted other than vertically; i.e., a pipeline reactor.

The solids concentration in the reaction zone of the reactor can range from, typically, about 1 lb/ft$^3$ (16 kg/m$^3$) to, typically, about 40 lb/ft$^3$ (640 kg/m$^3$), depending on the gas velocity, solids particle size and density, and the solids circulation rate. Preferably, the solids flux (mass flow rate per unit area) is at 2.1 to 42 lbs•ft$^{-2}$sec$^{-1}$ (10.2 to 204 kg•m$^{-2}$•sec$^{-1}$).

Figure 1:
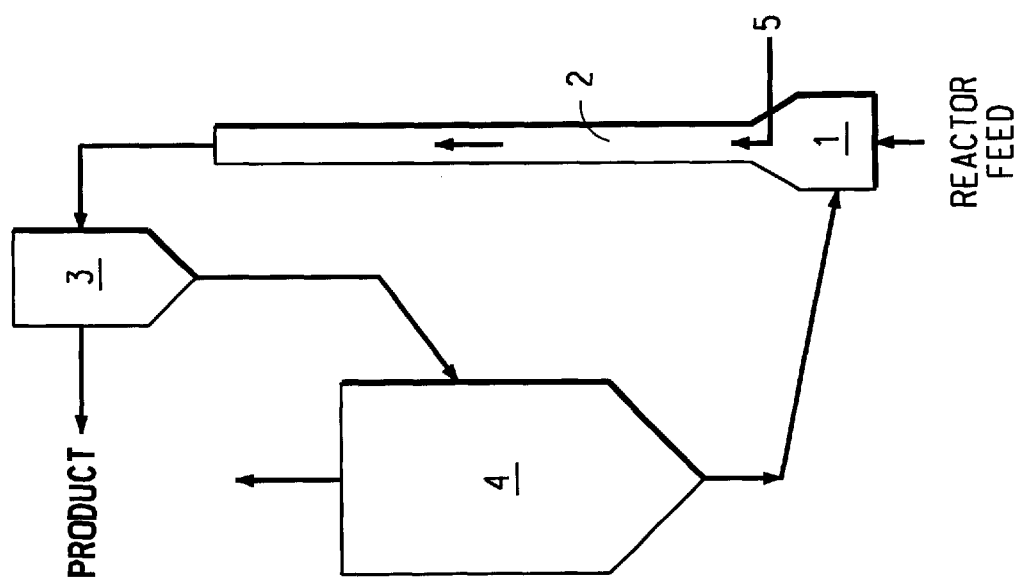
FIG. 1 shows a schematic drawing of a recirculating solids reactor configuration in which the reaction zone is comprised of two parts, a fluid bed section and a riser section and the regeneration zone is comprised of a fluid bed section.

FIG. 1 is a schematic drawing of one of the recirculating solids reactor systems used in the example. The reaction zone is comprised of a fluidization section 1 and a riser section 2. The feed gas enters 1 and the oxidation of propylene takes place in sections 1 and 2. The separator-stripper unit 3 separates and strips off the reaction zone effluent gases from the reduced solids. The acrylic acid and optionally acrolein product is recovered from the reactor effluent gases leaving 3. The reduced solids is transported to the regeneration zone which is comprised of the fluidized bed section 4. The reduced solids are oxidized in section 4 and the oxidized (regenerated) solids are then recycled to the fluidization section 1. The alternate/additional feed line 5 can be used to feed additional oxygen or oxygen containing gas, propylene, or recycle gases to riser section 2. The recirculation solids reactor of this embodiment can also be operated with just the riser section 2 as the reaction zone. In this mode of operation the feed can be introduced into the riser section 2 through feed line 5.

FIG. 2 is a schematic drawing of another recirculating solids reactor system. The reaction zone is comprised of a riser section 11. The feed gas enters 11 and the oxidation of propylene takes place in 11. The separator-stripper unit 12 separates and strips off the reaction zone effluent gases from the reduced solids. The acrylic acid and optionally acrolein product is recovered from the reactor effluent gases leaving 12. The reduced solids are transported to the regeneration zone which is comprised of a riser section 13 and a fluidized bed section 14. The reduced solids are oxidized in this regeneration zone and the oxidized (regenerated) catalyst is then recycled to the riser section 11.

The reaction and regeneration zones can be within a single reactor, although better process control usually is achieved if the two are in separate units.

The conversion of propylene in percent is defined as 100 times the number of mols of propylene converted, divided by the number of mols of propylene in the feed. The selectivity to acrylic acid and acrolein in percent is defined as 100 times the number of mols of propylene converted to these products divided by the total number of mols of propylene converted. The yield of acrylic acid and acrolein in percent is defined as 100 times the number of mols of acrylic acid and acrolein formed divided by the number of mols of propylene in the feed.

As indicated previously, there are a number of bismuth molybdate oxidants disclosed in the art as suitable for the oxidation of propylene to acrolein. Likewise there are a number of molybdenum vanadate type oxidants disclosed in the art as suitable for the oxidation of acrolein to acrylic acid. The process of this invention is not limited to a particular method of making these oxidants, nor to a particular promoter; i.e., oxidants known in the art to contain surface labile oxygen capable of converting propylene to acrolein and/or acrolein to acrylic acid. It should be further appreciated that other transition metal oxidant system known in the art to promote either the oxidation of propylene to acrolein or acrolein to acrylic acid, such as for example but not by way of limitation the iron/anitimony metal oxide solids, should be considered equivalent for purposes of the process of the present invention.

The multimetal solids used in the various runs of the Example of this invention were prepared by substantially following the procedure in U.S. Pat. No. 4,769,477, particularly the procedure of Example 10 wherein the multimetal solid component was slurried with sufficient polysilicic acid solution to result in typically 10 wt % $SiO_2$ in the final dry solids prior to spray drying and subsequent calcining or by substantially following a related procedure in U.S. patent application Ser. No. 09/088,804 filed on Jun. 2, 1998, wherein sufficient colloidal silica solution was added to the slurry of the multimetal solid component and polysilicic acid to result in an additional 30 wt % $SiO_2$ in the final dry solids again prior to spray drying and subsequent calcining. The use of the expression "substantially following the procedures" is not intended as an implication that the same ingredients were employed, but rather that the same general techniques were used to achieve attrition resistance starting with the two types of solids; i.e., bismuth molybdate multimetal solids and molybdenum vanadate multimetal solids, respectively.

In the Example, the bismuth molybdate multimetal starting solids were obtained following the procedure described in French patent application 97 02343 filed on Feb. 27, 1997 in the name of Elf Atochem S.A., "Method for the Manufacture of Acrolein from Propylene by Redox Reaction and use of a Solid Mixed Oxide Compositions as Redox System in the Said Reaction". More specifically, the bismuth molybdate starting solids used in the runs of the Example of this invention were obtained according to example 5 of this French patent application. These starting solids correspond to the formula: $Mo_{12}Co_{3.5}Bi_{1.1}Fe_{0.8}W_{0.5}Si_{1.4}K_{0.05}O_x$; where x is the quantity of oxygen bonded to the other elements and depends on their oxidation state. The procedure involved 60.9 grams of $Co(NO_3)_2 \cdot 6H_2O$ being dissolved in 20 mL of distilled water. Also, 20.2 grams of $Fe(NO_3)_3 \cdot 9H_2O$ were dissolved in 15 mL of distilled water and 31.2 grams of $Bi(NO_3)_3 \cdot 5H_2O$ were dissolved in 30 mL of distilled water acidified with 6 mL $HNO_3$ at a concentration of 68% by volume. Separately 127.4 grams of $(NH_4)_6Mo_7O_{24} \cdot 4H_2O$ were dissolved in 150 mL of water with heating and stirring and then 7.4 grams of $WO_3$ were added. The aqueous solution containing the cobalt was introduced dropwise over 20 minutes into the aqueous solution of the ammonium salts. The ferric solution was next introduced over 10 minutes and then the solution containing the bismuth over 15 minutes. A solution obtained by dissolving 0.2 grams of KOH and 12.8 grams of colloidal silica (at a concentration of 40 weight %) in 15 mL of water was added over 10 minutes resulting in gel formation. The gel thus obtained was blended for 1 hour at ambient temperature and then 1 hour at 70° C. The gel was next dried for 18 hours at 130° C. to obtain a solid precursor. The solid obtained was precalcined at 225° C. in air and milled. Before calcination at 450° C. for 9 hours in air, this solid precursor corresponding to the above formula was then mixed with polysilicic acid solution as described in Example 10 of the U.S. Pat. No. 4,677,084 (to impart either 10 or 12 wt % silica in the final dry solids with the remaining 90 or 88%, respectively, being the bismuth molybdate multimetal oxide component) and further treated to produce the attrition resistant bismuth molybdate multimetal oxide component of the oxidant mixture used in the following runs 1 through 8 of the Example.

The molybdenum vanadate multimetal starting solids were obtained according to EXAMPLE 1(a) of French patent application 97 02344 filed on Feb. 27, 1997 in the name of Elf Atochem S.A., "Process for Manufacture of Acrylic Acid from Acrolein by Redox Reaction and use of a Solid Mixed Oxide Composition as Redox System in the Said Reaction". These starting solids correspond to the formula. $Mo_{12}V_{4.8}Sr_{0.5}W_{2.4}Cu_{2.2}O_x$; where x is the quantity of oxygen bonded to the other elements and depends on their oxidation state.

The procedure involved 3.6 grams of ammonium paratungstate, 3.0 grams of ammonium metavanadate and 12.4 grams of ammonium heptamolybdate being introduced into 100 grams of water and heated to 100° C. Also, 3.0 grams of copper nitrate and 0.62 grams of strontium nitrate were introduced into 5 grams of water and heated to 100° C. The second solution was added to the first and the resulting slurry was then evaporated to dryness. The solids were precalcined at 225° C. in air to produce the desired precursor. Before calcining 400° C. for 4 hours in air, this solid precursor corresponding to the above formula was then mixed with polysilicic acid solution as described in Example 10 of the U.S. Pat. No. 4,677,084 (to impart at least 10 wt % silica, see Run 4 of the example) or mixed with polysilicic acid solution and a colloidal silica solution as described in U.S. patent application Ser. No. 09/088,804 to impart 10% silica from the polysilicic acid and 30% silica from the colloidal silica with the remaining 60% being the molybdenum vanadate multimetal component (see Runs 1–3 and 5–8 of the Example) and further treated to produce the attrition resistant molybdenum vanadate multimetal oxide component of the oxidant mixture.

The following example with several individual runs is presented to more fully demonstrate and further illustrate various individual aspects and features of the present invention. As such the examples are felt to be non-limiting and are meant to illustrate the invention but are not meant to be limiting in any way.

EXAMPLE

A recirculating solids reactor system of the type shown in FIG. 1 was used to oxidize propylene to acrylic acid in a single step. The transport bed reactor consisted of a small fluidization section surmounted by a ⅝ inch (1.59 cm) diameter by 10 foot (3.05 m) tall riser tube. The recirculating mixture of solids was transported up the riser tube with the reactant and product gases which are in plug flow. Reactant gas contact times were on the order of 1 to 5 seconds. Isothermal conditions (approximately 336±4° C.) were maintained by an electric furnace. Reactor pressure was maintained at 1 to 2 psig ($6.89 \times 10^3$ to $1.38 \times 10^4$ Pa) at the top of the riser. Riser superficial gas velocity was in the range of 6.6 to 10.5 ft/sec (2.67 to 3.02 m/sec). Riser gas contact time was in the range of 0.9 to 1.5 seconds. Propylene and acrolein feed concentrations were varied as shown in the following Table 1. Steam feed concentrations were in the range of 5 to 22.5 mol %. All feed flows were controlled by thermal mass flow controllers. Propylene and nitrogen were fed to the fluidization zone.

The product gas stream leaving the riser was separated from the solids in a two stage cyclone separator and fed to the product quench/absorption system. The solids from the separator were transported to the regenerator via a 4 inch (10 cm) diameter fluidized bed stripper.

The regenerator was a 4.5 inch (11.4 cm) diameter fluidized bed. Solids bed height (solids contact time) in the regenerator was controlled by differential pressure control between the stripper and regenerator. Air was fed to the regenerator to re-oxidize the solids. The off-gas from the regenerator was fed to the regenerator quench system after disengagement from the solids in a series of cyclones.

From the regenerator, the oxidized catalyst was then fed back to the fluidization section of the transport bed reactor. The solids circulation rate was in the range of 15 to 30 kg/hr.

The two quench systems for the product and regenerator off-gases were of identical design. A recirculating liquid served as a direct contact condenser/absorber for the products. Caustic was used on the product off-gas to absorb organic products and to neutralize the acrylic acid produced. Water was used on the regenerator off-gas.

A hot gas sample stream for the product off-gas was taken to two static water absorbers. The first was used to absorb $C_2/C_3$ aldehydes and acids for quantitative analysis by an off-line gas chromatograph. The second was used as a pre-treatment absorber to remove aldehydes and acids which interfere with the analysis, prior to on-line gas chromatographic analysis of $N_2$, $O_2$, propylene, CO and $CO_2$.

The regenerator off-gas was sampled down-stream of the water quench and analyzed for $N_2$, $O_2$, propylene, CO and $CO_2$. Reactor performance was determined by on-line gas chromatograph analysis for non-absorbed components in each of the two off-gas streams. Water absorbed products were measured by off-line gas chromatograph analysis of the liquid sample absorber.

The primary process variables in the tables below are defined as follows: Fluid. Bed Temp ° C. (fluidized bed temperature in ° C.); $C_3H_6$ Feed Conc. (propylene feed concentration in mol %); Acrolein Feed Conc.(acrolein feed concentration in mol %); Steam Feed Conc. (steam feed concentration in mol %); Oxygen Feed Conc. (oxygen feed concentration in mol %); Riser Gas Cont.Time (riser gas contact time in seconds); Fluid. Bed Gas Cont.Time (fluidized bed gas contact time in seconds); Sol.Circ.Rate kg/hr (solids circulation rate in kilograms per hour); Mo—V/(Mo—V+Bi—Mo) Catal. in Chg (Wt %) (Molybdenum Vanadate type solids wt %, i.e. the weight percent of total charge with the remainder being bismuth molybdate multimetal oxide).

The primary responses were measured as key process variables were changed. These primary responses are defined as follows: Riser $C_3H_6$ Conver. % (riser propylene conversion %); Acrol.+Acrylic Select. % (selectivity based on the sum of acrolein and acrylic acid selectivities); Acrylic acid Select. % (selectivity to acrylic acid only); $C_2$ Select. % (selectivity to acetic acid and acetic anhydride); $CO_x$ Select. % (selectivity to CO and $CO_2$); and Sol. Conver. Ratio kg/kg (solids conversion ratio; i.e., kg solids circulated/kg propylene converted). Table 1 summarizes the data associated with runs 1 through 8.

TABLE 1

SINGLE STEP ⅝ INCH RISER TEST:
ALL REACTANT FEEDS TO FLUIDIZED BED

| | PROCESS CONDITIONS | | | | | | | |
|---|---|---|---|---|---|---|---|---|
| Run No. | 1 | 2 | 3 | 4 | 5 | 6 | 7 | 8 |
| Fluid. Bed Temp ° C. | 332 | 337 | 335 | 335 | 337 | 337 | 332 | 340 |
| $C_3H_6$ Feed Conc. | 20.8 | 20.0 | 19.2 | 15.0 | 20.0 | 20.0 | 20.0 | 20.0 |
| Acrolein Feed Conc. | 0.00 | 0.00 | 0.00 | 0.00 | 1.86 | 2.79 | 0.93 | 1.86 |

TABLE 1-continued

| Steam Feed Conc. | 11.9 | 5.6 | 22.5 | 20.1 | 20.2 | 20.2 | 20.2 | 20.2 |
|---|---|---|---|---|---|---|---|---|
| Oxygen Feed Conc. | 0.01 | 4.39 | 3.76 | 0.00 | 0.00 | 0.00 | 0.00 | 0.00 |
| Riser Gas Cont. Time | 1.0 | 0.9 | 1.2 | 1.2 | 1.2 | 1.2 | 1.2 | 1.2 |
| Fluid Bed Gas Cont.Time | 0.5 | 0.5 | 0.7 | 0.7 | 0.7 | 0.7 | 0.7 | 0.7 |
| Sol.Circ.Rate(kg/hr) | 27 | 24 | 15 | 30 | 20 | 21 | 22 | 22 |
| Mo—V/(Mo—V + Bi—Mo) Sol.in Chg(wt%) | 15[a] | 15[a] | 10[a] | 12[b] | 20[a] | 20[a] | 20[a] | 20[a] |

[a] Mo—V is 60% active molybdenum vanadate component and 40% silica and Bi—Mo is 90% active bismuth molybdate component and 10% silica.
[b] Mo—V is 90% active molybdenum vanadate component and 10% silica and Bi—Mo is 88% active bismuth molybdate component and 12% silica.

RESPONSES

| Riser $C_3H_6$ Conver. % | 6 | 11 | 16 | 10 | 11 | 12 | 12 | 13 |
|---|---|---|---|---|---|---|---|---|
| Acrol.+ Acrylic Select.% | 76 | 77 | 76 | 77 | 78 | 81 | 82 | 78 |
| Acrylic Acid Select.% | 46 | 50 | 50 | 20 | 78 | 81 | 62 | 78 |
| $C_2$ Select.% | 6 | 4 | 5 | 5 | 4 | 4 | 4 | 5 |
| $CO_x$ Select.% | 17 | 17 | 19 | 17 | 17 | 15 | 14 | 17 |
| Sol.Conv.Ratio kg/kg | 1190 | 566 | 348 | 1486 | 636 | 583 | 660 | 575 |

The above results confirm the feasibility of conversion of propylene to acrylic acid in a single step and at low selectivity to $C_2$ and $CO_X$ using a mixture of a molybdenum vanadate multimetal oxide and a bismuth molybdate multimetal oxide as oxidant. With some acrolein feed to the reactor zone, acrylic acid selectivities are increased substantially by limiting propylene exposure and $CO_X$ formation on the molybdenum vanadate multimetal oxide. This points to an advantage for acrolein (and propylene) recycle to the reaction zone, which is a likely operating mode on a commercial scale.

Having thus described and exemplified the invention with a certain degree of particularity, it should be appreciated that the following claims are not to be so limited but are to be afforded a scope commensurate with the wording of each element of the claim and equivalents thereof.

We claim:

1. A process for the oxidation of propylene to acrylic acid comprising the steps of:

(a) contacting a feed gas comprising (i) from 1 to 100 mol % propylene, (ii) from 0 to 20 mol % oxygen, (iii) from 0 to 70 mol % water, and (vi) the remainder inert gas with an effective amount of an oxidant mixture comprising a particulate molybdenum vanadate multimetal oxide in an oxidized state and a bismuth molybdate multimetal oxide in an oxidized state at a temperature from 250 to 450° C. and for a time sufficient to convert a portion of said propylene to acrylic acid, wherein the relative amount of said molybdenum vanadate multimetal oxide is from 5 to 50 percent by weight total active ingredients and the remainder 95 to 50 percent by weight is said bismuth molybdate multimetal oxide; and (b) recovering said acrylic acid produced in step (a).

2. A process of claim 1 wherein said contacting of said feed gas and said particulate oxidant mixture in an oxidized state such as to convert said propylene to acrylic acid is performed in a transport bed reactor of a recirculating solids reactor system and wherein said particulate oxidant mixture in a reduced state after said conversion of propylene to acrylic acid is separated from said acrylic acid gaseous product and is then reoxidized in a regenerator reactor of said recirculating solids reactor system by contact with oxygen containing gas before being recirculated to said transport bed reactor.

3. A process of claim 2 wherein said transport bed reactor is a riser reactor and wherein said particulate oxidant mixture comprises particles from 10 to 300 micron in size.

4. A process of claim 3 wherein said feed gas residence time in said riser reaction zone is from 1 second to about 15 seconds, and said particulate oxidant mixture residence time in said riser reaction zone is from 2 seconds to 120 seconds.

5. A process of claim 3 said particulate oxidant mixture residence time in said regenerator reactor is from 0.5 minute to 10 minutes, and at an oxygen-containing gas residence time of 3 seconds to 30 seconds at a temperature of about 250 to about 500° C.

6. A process of any one of the preceding claims 1 through 5 wherein said molybdenum vanadate multimetal oxide corresponds to the formula: $Mo_{12}V_{4.8}Sr_{0.5}W_{2.4}Cu_{2.2}O_x$ where x is the quantity of oxygen bonded to the other element according to their respective oxidation states.

7. A process of any one of the preceding claims 1 through 5 wherein said bismuth molybdate multimetal oxide corresponds to the formula $Mo_{12}Co_{3.5}Bi_{1.1}Fe_{0.8}W_{0.5}Si_{1.4}K_{0.05}O_x$ where x is the quantity of oxygen bonded to the other elements according to their respective oxidation states.

8. A process of any one of the preceding claims 1 through 5 wherein said multimetal oxides are obtained by mixing of metal salts, drying said mixture and then precalcining said dry mixture at 225° C. or above in air.

* * * * *